(12) United States Patent
Chen

(10) Patent No.: US 8,388,244 B2
(45) Date of Patent: Mar. 5, 2013

(54) ELEVATION DEVICE OF MONITORING CAMERA

(75) Inventor: Jun-Ching Chen, Taipei (TW)

(73) Assignee: Chao-Ying Kuo, Taipei (TW)

(*) Notice: Subject to any disclaimer, the term of this patent is extended or adjusted under 35 U.S.C. 154(b) by 376 days.

(21) Appl. No.: 12/764,981

(22) Filed: Apr. 22, 2010

(65) Prior Publication Data

US 2010/0284682 A1    Nov. 11, 2010

(30) Foreign Application Priority Data

May 8, 2009    (TW) ................... 98207893 U

(51) Int. Cl.
G03B 17/02    (2006.01)
G03B 17/58    (2006.01)

(52) U.S. Cl. ....................... 396/427; 248/320

(58) Field of Classification Search ............ 396/427; 248/320, 328
See application file for complete search history.

(56) References Cited

U.S. PATENT DOCUMENTS

| | | | | |
|---|---|---|---|---|
| 1,454,855 A * | 5/1923 | Larkins | ............... | 248/320 |
| 3,038,125 A * | 6/1962 | Koster | ............... | 330/92 |
| 4,115,845 A * | 9/1978 | Blahut | ............... | 362/403 |
| 4,149,230 A * | 4/1979 | Garchinsky | ............... | 362/403 |
| 7,303,182 B2 * | 12/2007 | Ash | ............... | 254/336 |
| 2010/0051767 A1 * | 3/2010 | Erel et al. | ............... | 248/205.1 |

* cited by examiner

Primary Examiner — Clayton E LaBalle
Assistant Examiner — Leon W Rhodes, Jr.
(74) Attorney, Agent, or Firm — Leong C. Lei

(57) ABSTRACT

An elevation device is provided for a monitoring camera, including a top retaining barrel fixed to the top end of a high suspending post and downward fit onto a retained member. The retained member has a bottom forming the wire box. A retained cylinder has an outer circumference forming spaced locking blocks. The top retaining barrel comprises a locking tube receiving therein a toothed crown locking collar that comprises oppositely set first and second toothed crowns between when the locking blocks are movable to alternately carry out locking and unlocking operation. The locking tube forms a guide block corresponding to an inclined circumferential surface of a cam, whereby when the retained cylinder is driven upward in any orientation to fit into the locking tube, the inclined circumferential surface is guided by the guide block to correct orientation of the retained cylinder with respect to retained cylinder.

12 Claims, 7 Drawing Sheets

US 8,388,244 B2

ELEVATION DEVICE OF MONITORING CAMERA

TECHNICAL FIELD OF THE INVENTION

The present invention generally relates to an elevation device of monitoring camera, which provides a novel structure that allows suspension on a coupling device set at a top end of a high suspending post through a steel cable so that there is no need for an operator to climb high and the operator may readily lower and raise the device on the ground for carrying out maintenance and repairing.

DESCRIPTION OF THE PRIOR ART

Devices with high suspending posts, such as a speeding monitor camera installed by a high way, require an operator to climb up to the top of the post to access the related components for carrying maintenance and repairing. Although tower structures that allow easy gripping and climbing are now used to construct an installation base, climbing is still an effort- and time-consuming job and is also dangerous and more time is spent in climbing than carrying out the maintenance and repairing operation of the output/input components. An operator can only serve a very limited number of the high suspending posts. This is not only low in efficiency, but also making the maintenance cost very high and is also risky for injury to the operator when he or she accidentally falls down.

In view of the drawbacks of the conventional high suspending posts where an operator must climb high for performing maintenance, the present invention aims to provide a solution to such a problem.

SUMMARY OF THE INVENTION

The primary purpose of the present invention is to provide an elevation device of monitoring camera, which comprises a top retaining barrel that is fixed to the top end of the high suspending post and downward fit onto a retained member. The retained member has a bottom forming the wire box. A retained cylinder, which has an opening receiving and fixing a steel cable therein, is erected on a top center of the wire box. The retained cylinder has an outer circumference on which a plurality of locking blocks is circumferentially arranged in an equally spaced manner at a location close to the opening and at a proper altitude. A raised cam, which has an inclined circumferential top surface, is formed on a portion of the outer circumference of the retained cylinder between the wire box and the locking blocks. The top retaining barrel comprises a locking tube set at a center thereof. The locking tube receives therein a toothed crown locking collar at a location corresponding to a push position of the locking blocks that is defined at the time when the retained cylinder is almost fully inserted for being driven by the locking blocks in a tooth-by-tooth fashion to slide in a single given direction so as to alternately carry out locking and unlocking operation on the locking blocks. The locking tube forms a raised guide block on an inside surface thereof at a location adjacent to a bottom opening and corresponding to the inclined lower portion of the inclined circumferential top surface, whereby when the retained cylinder is pulled upward in any orientation to fit into the locking tube, the inclined circumferential top surface is guided by the guide block to correct orientation of the retained cylinder with respect to retained cylinder so that further pulling moves the retained cylinder to an uppermost position to be retained and locked, by which the camera is selectively and readily raised and lowered by an operator staying on ground without climbing high to proceed with maintenance and repairing of the camera. Thus, the risk of the operator falling down and hurt can be eliminated.

Further, the elevation device of monitoring camera of the present invention is operated by being pulled by an operator on the ground to have the components moved up and down for carrying out maintenance and repairing. The total weight of the present invention is far less than the body weight of the operator so that the force and effort that the operator spends in pulling and controlling the descending of the present invention is far less than raising his or her own body weight up the post suspending the camera. Thus, the number of camera suspending posts that an operator may serve in every day is increased, which leads to an increase of efficiency of maintenance. This is another objective of the present invention.

Further, the elevation device of monitoring camera of the present invention provides an apparent and outstanding improvement on efficiency, safety, and convenience for maintenance and repairing of high raised components, through which electrical facility installed on high suspending posts can be made with lower maintenance and repairing costs for long term operation. This is a further objective of the present invention.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
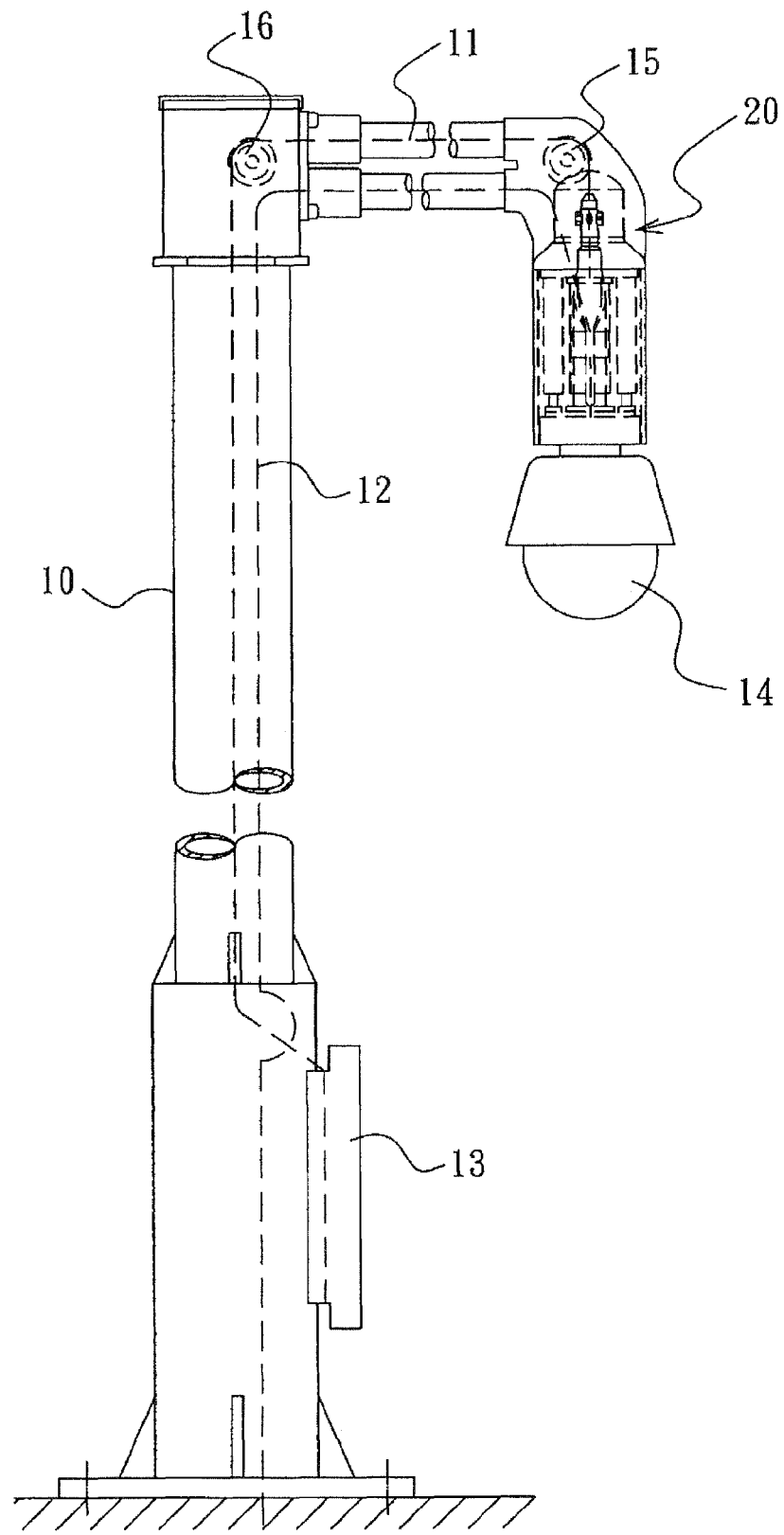
FIG. 1 is a schematic view illustrating a high suspending post for the installation of an elevation device of monitoring camera in accordance with the present invention.
Figure 2:
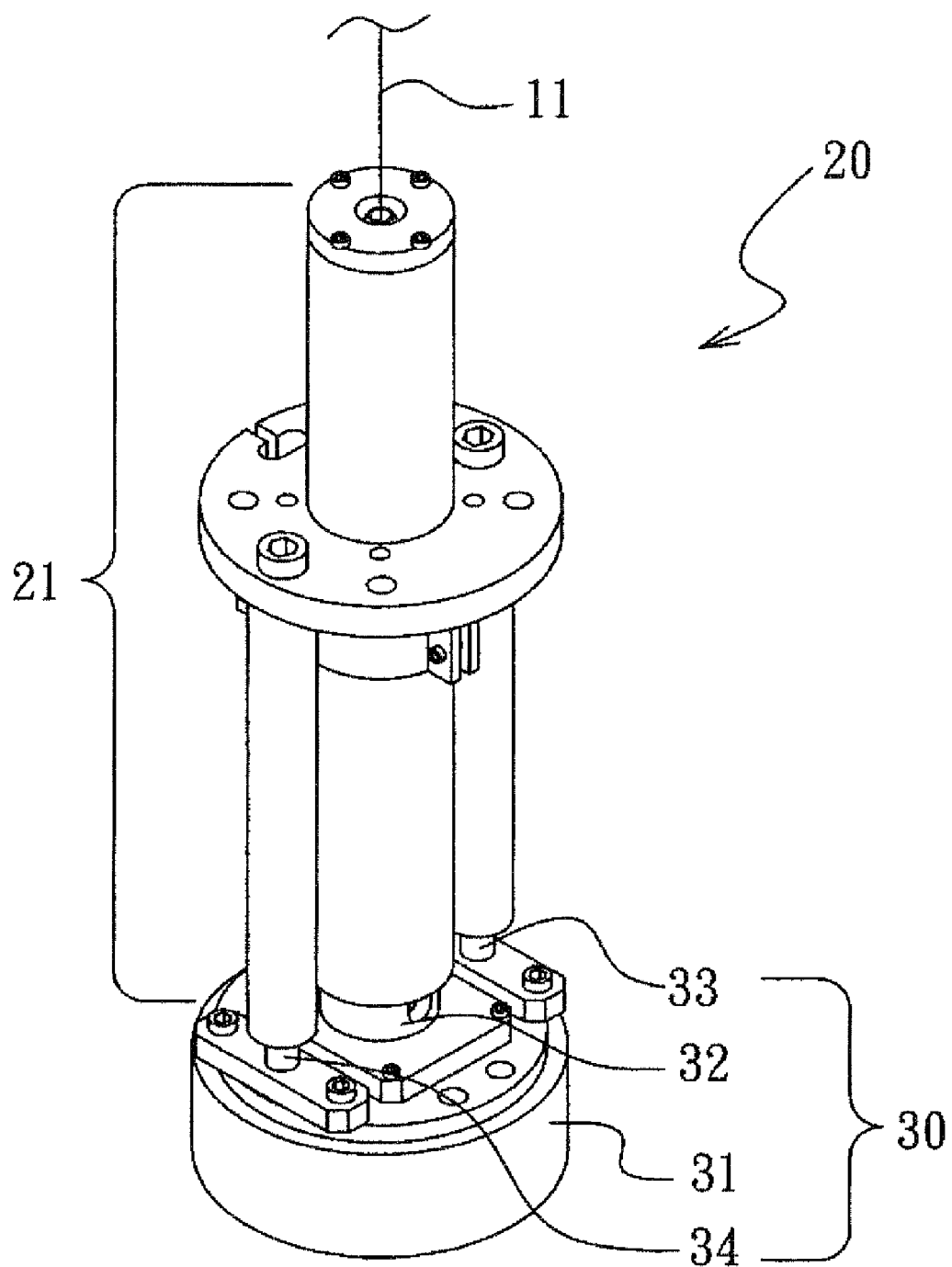
FIG. 2 is a perspective view of the present invention.

FIG. 1 is a schematic view illustrating installation of an elevation device of monitoring camera in accordance with the present invention. Reference is also made to FIG. 2, which is a perspective view of the elevation device. In these drawings, reference numeral 14 indicates a camera, of which a highway monitoring camera is taken as an example for explanation. From these drawings, it is shown that the elevation device 20 of monitoring camera in accordance with the present invention, which is hung on a top end of a high suspending post 10 by a steel cable 11 that is set in a curved arrangement and has a bottom to which a wire box 31 of a camera 14 is mounted, serves as a coupling for securing the camera 14 that is arranged on the top end of the high suspending post 10 and suspended on the top end of the high suspending post with a curved arrangement of the steel cable 11. The steel cable 11 extends through a post body of the post 10 in a manner of being sideways shifted off a transmission cable 12 set inside the post 10, passes around fixed pulleys 15, 16, and projects outside a base of the post 10 for being wound around and attached to a winching mechanism 13 set beside the base of the post 10.

Figure 3:
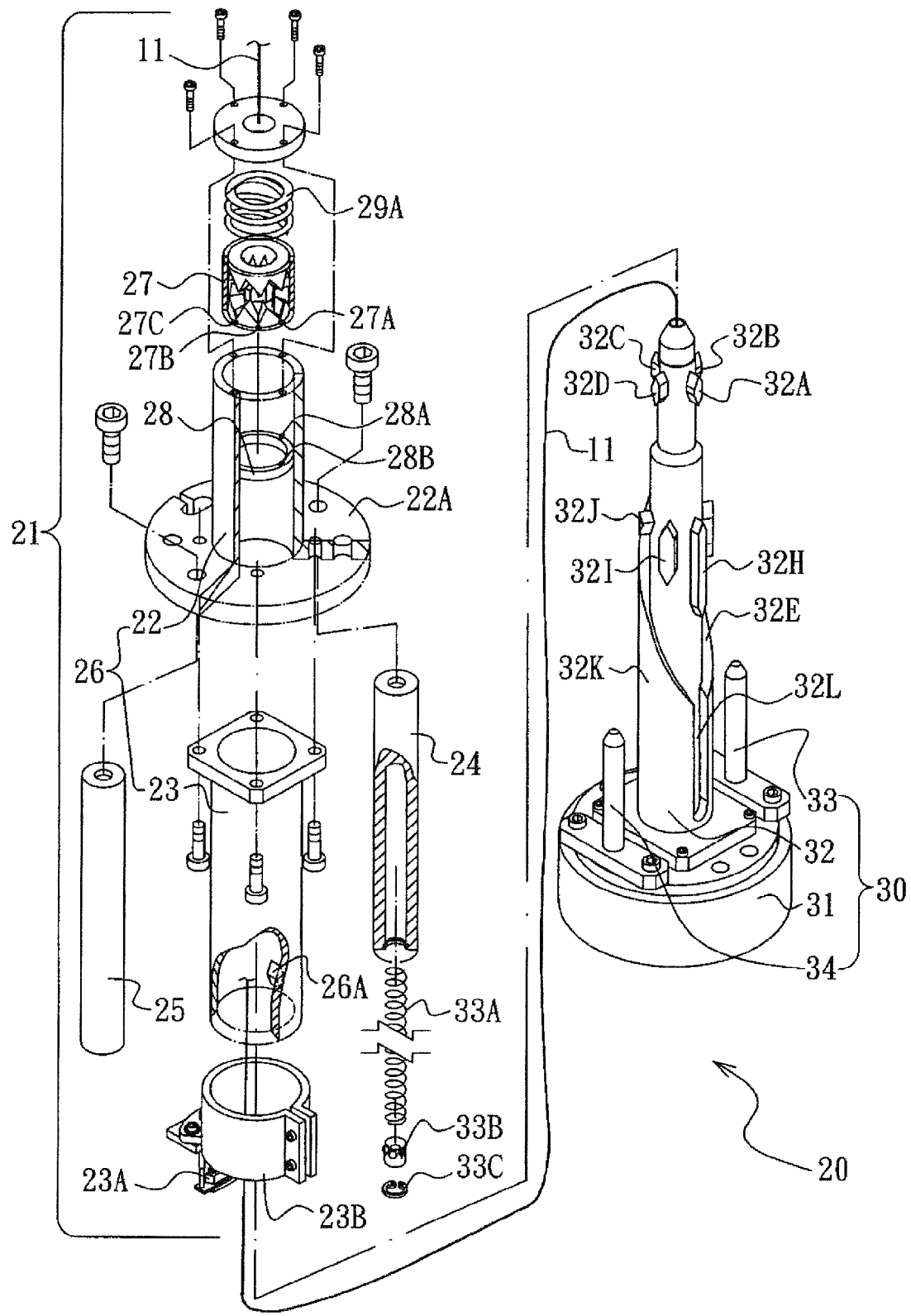
FIG. 3 is an exploded view of FIG. 2.

The elevation device 20 of monitoring camera, which has a detailed structure illustrated in an exploded view of FIG. 3, is composed of a top retaining barrel 21 that is bolted to the top end of the high suspending post 10 shown in the previously discussed drawings and downward fit onto a retained member 30. The retained member 30 has a bottom forming the wire box 31. A retained cylinder 32, which has an opening receiving and fixing the steel cable 11 therein, is erected on a top center of the wire box 31. Two positioning bars 33, 34 vertically extend from the top of the wire box 31 at positions on opposite sides of and spaced from the retained cylinder 32 by equal distance. The retained cylinder 32 has an outer circumference on which a plurality of locking blocks 32A, 32B, 32C, 32D is circumferentially arranged in an equally spaced manner at a location close to the opening and at a proper altitude. The locking blocks 32A, 32B, 32C, 32D are of a configuration having upper and lower ends that are converging and sharp, having apexes sideways shifted by a predetermined amount. A raised cam 32K having an inclined circumferential top surface 32E is formed on a portion of the outer circumference of the retained cylinder 32 between the wire box 31 and the locking blocks 32A, 32B, 32C, 32D. The inclined circumferential top surface 32E has an inclined lower portion that forms in a downward direction a vertical slot 32L. A plurality of circumferentially distributed vertical ribs 32H, 32I, 32J, which has upper and lower end that are converging and sharp, is formed on the retained cylinder 32 at an end thereof opposite to the inclined circumferential top surface 32E.

The top retaining barrel 21 is constructed by bolting a bottom of a hollow suspension locking cylinder 22 to a hollow connection cylinder 23 and a pair of resilient push tubes 24, 25. The suspension locking cylinder 22 is provided with a mounting flange 22A that projects from a bottom circumference of the suspension locking cylinder 22 for being bolted to the top end of the high suspending post 10 shown in the previously discussed drawings. The flange 22A is also downward bolted to the connection cylinder 23 and the pair of resilient push tubes 24, 25 in such a way that the cylinder 23 is in alignment with the suspension locking cylinder 22 to constitute together a locking tube 26 that is set at the center of the top retaining barrel 21. The locking tube 26 receives therein a toothed crown locking collar 27 at a location corresponding to a push position of the locking blocks 32A, 32B, 32C, 32D that is defined at the time when the retained cylinder 32 is almost fully inserted for being driven by the locking blocks 32A, 32B, 32C, 32D in a tooth-by-tooth fashion to slide in a single direction so as to alternately carry out locking and unlocking operation on the locking blocks 32A, 32B, 32C, 32D. The tube 26 forms therein a support flange 28 that projects inwardly to correspond to a bottom of the collar 27. The flange 28 forms a number of circumferentially arranged raised bosses 28A, 28B and the collar 27 forms in a bottom thereof a plurality of circumferentially arranged notches 27A, 27B, 27C, of which the number is two times of that of the bosses 28A, 28B and is engageable with the bosses 28A, 28B. A spring 29A is set between the collar 27 and an inside wall of a top opening of the locking tube 26. The locking tube 26 forms on an inside surface thereof at a location adjacent to a bottom opening and corresponding to the inclined lower portion of the inclined circumferential top surface 32E a raised guide block 26A that has upper and lower ends both being converging and sharp and has a width slidably receivable into the vertical slot 32L. The pair of resilient push tubes 24, 25 has openings aligning the positioning bars 33, 34 respectively and each sequentially receives therein a spring 33A and a linear bearing 33B. An inner retention ring 33C is mounted inside the tube opening so that the linear bearing 33B and the spring 33A are retained and prevented from springing out of the tube opening by the inner retention ring 33C. An end of the positioning bar 33 is allowed to extend through the linear bearing 33B to compress the spring 33A. A downward-oriented connector 23A has a clamp ring 23B fit over an outer circumference of the connection cylinder 23 at a location close to the mounting flange 22A.

Figure 4:
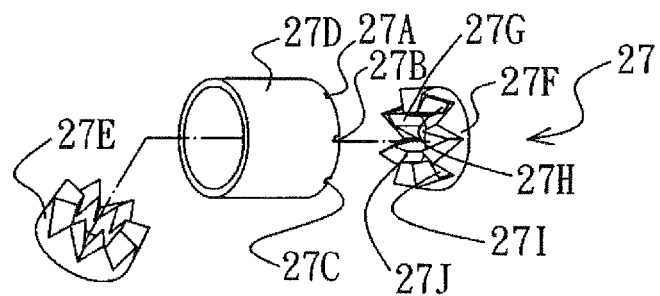
FIG. 4 is an exploded view of a toothed crown locking collar of FIG. 2.
Figures 5, 6:
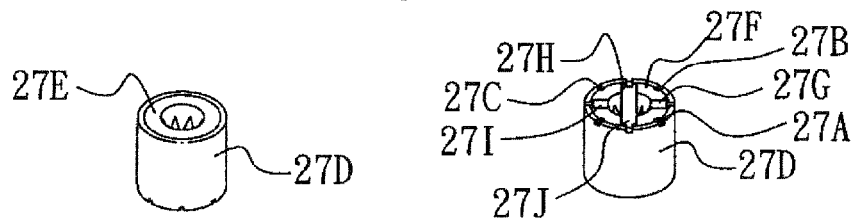
FIG. 5 is a top side perspective view of the toothed crown locking collar of FIG. 2.
FIG. 6 is a bottom side perspective view of the toothed crown locking collar of FIG. 2.

The toothed crown locking collar 27 has a detailed structure that will be explained with reference to FIG. 4, which is an exploded view of the toothed crown locking collar; FIG. 5, which is a top side perspective view of the toothed crown locking collar; and FIG. 6, which is a bottom side perspective view of the toothed crown locking collar. From these drawings, it is shown that the collar 27 is composed of a hollow collar cylinder 27D, a first toothed crown 27E, and a second toothed crown 27F, which are fixed together by means of for example welding. The collar cylinder 27D has a bottom in which the previously mentioned notches 27A, 27B, 27C are formed. The first toothed crown 27E and the second toothed crown 27F form teeth, which have apexes that are sideways shifted. The number of the teeth of each crown is two times of the number of the locking blocks 32A, 32B, 32C, 32D shown in the previous drawings. The teeth of each toothed crown 27E, 27F are circumferentially arranged and have such a thickness that forms a ring having a diameter sufficient to fit over an upper section of the retained cylinder 32. The second toothed crown 27F forms a channel 27G, 27H, 27I, 27J in an inside wall thereof corresponding to each alternate one of tooth troughs for allowing the locking blocks 32A, 32B, 32C, 32D to move therethrough. The first toothed crown 27E is set in a reversely oriented manner to fit into and close a top end of the collar cylinder 27D. The second toothed crown 27F is fit into and closes a bottom end of the collar cylinder 27D. The first toothed crown 27E and the second toothed crown 27F are arranged in such a way that the tooth apexes thereof are circumferentially shifted with respect to each other by a given distance, such as 2 mm, as shown in FIG. 3. The shifting amount of the apexes of the upper and lower converging and sharp ends of the locking blocks 32A, 32B, 32C, 32D, which was discussed with reference to the previous drawings, is set to allow the locking blocks 32A, 32B, 32C, 32D to abut against and slide along tooth flanks of the two toothed crowns 27E, 27F for moving up and down to switch between adjacent teeth for locking engagement so as to be secured by the teeth, or to withdraw through one of the channels 27G 27H, 27I, 27J for releasing.

Figure 7:
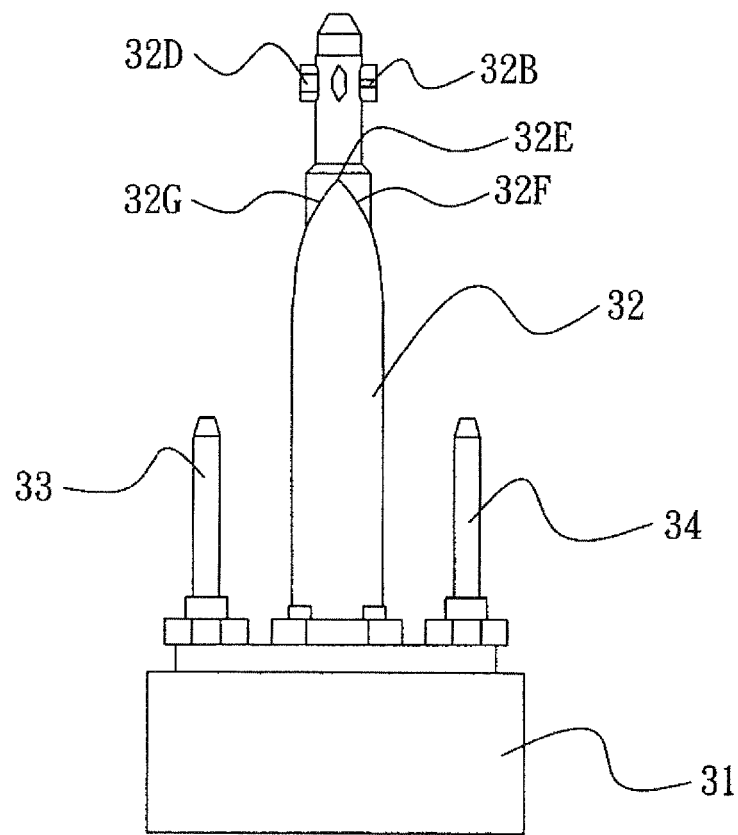
FIG. 7 is a back side view of a retained cylinder.
Figures 8, 9:
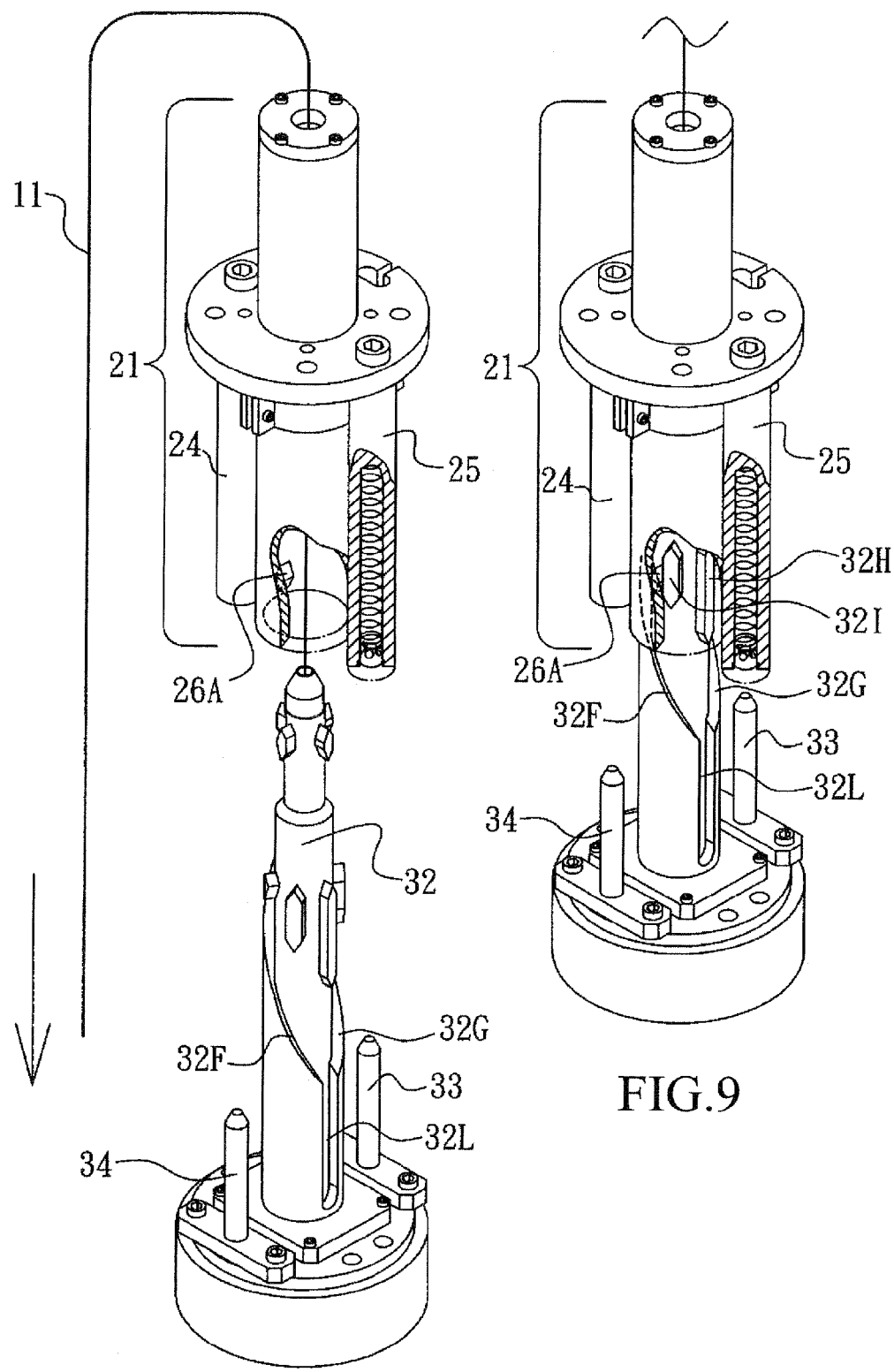
FIG. 8 is a schematic view showing the operation of the present invention in a first stage.
FIG. 9 is a schematic view showing the operation of the present invention in a next stage.

Further, from the back side view of the retained cylinder shown in FIG. 7, it is seen that the inclined circumferential top surface 32E formed by the retained cylinder 32 has a single tip point forming an apex that has opposite sides forming downward inclined guide faces 32F, 32G, whereby as shown in FIGS. 8 and 9, when the retained cylinder 32 is pulled upward to insert the retained cylinder 32 in an upward direction into the top retaining barrel 21, no matter in which direction it approaches the guide block 26A, one of the downward inclined guide faces 32F, 32G is guided and driven by the converging surfaces of the guide block 26A to induce rotation of the retained cylinder 32 in either a forward direction or a backward direction while the retained cylinder 32 is being raised, so as to set the retained cylinder 32 in a correct direction for being further pulled upward to have the positioning bars 33, 34 respectively fit into the resilient push tubes 24, 25 for establishing correct and stable coupling orientation.

Figure 10:
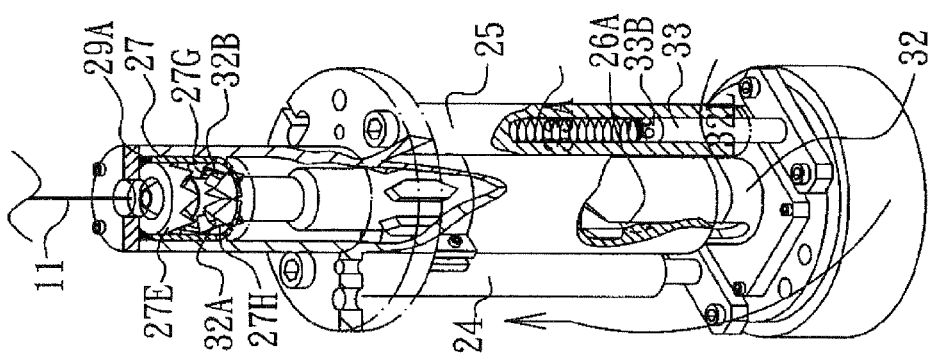
FIG. 10 is a schematic view showing the operation of the present invention in a further next stage.
Figure 11:
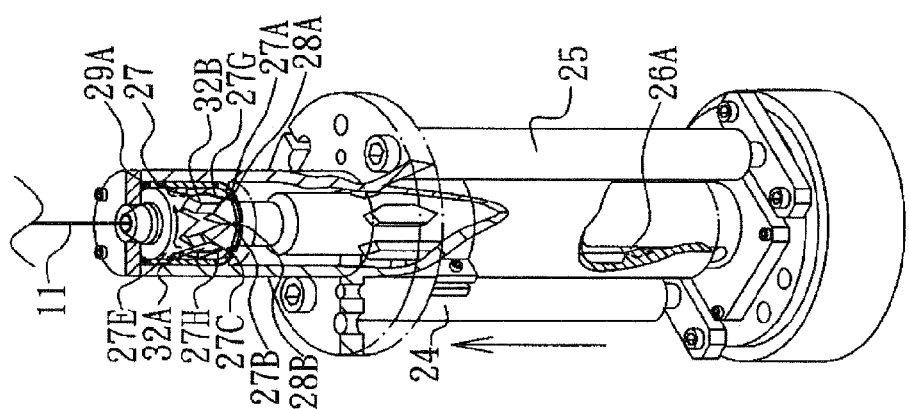
FIG. 11 is a schematic view showing the operation of the present invention in yet a further next stage.
Figure 12:
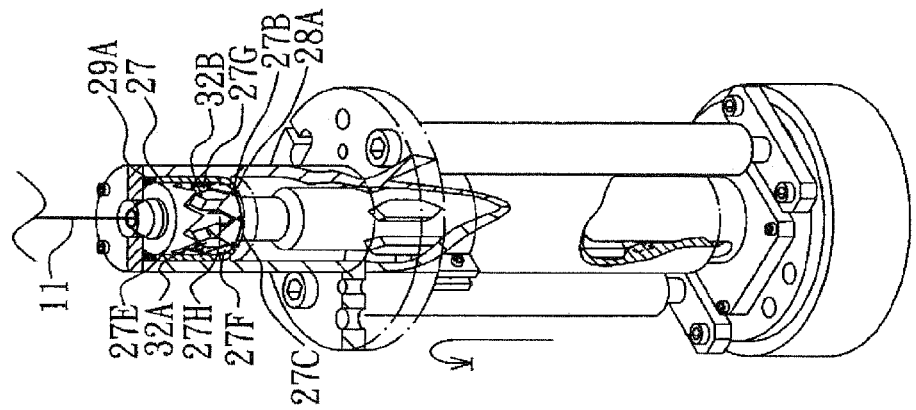
FIG. 12 is a schematic view showing the operation of the present invention in yet a further stage.
Figure 12A:
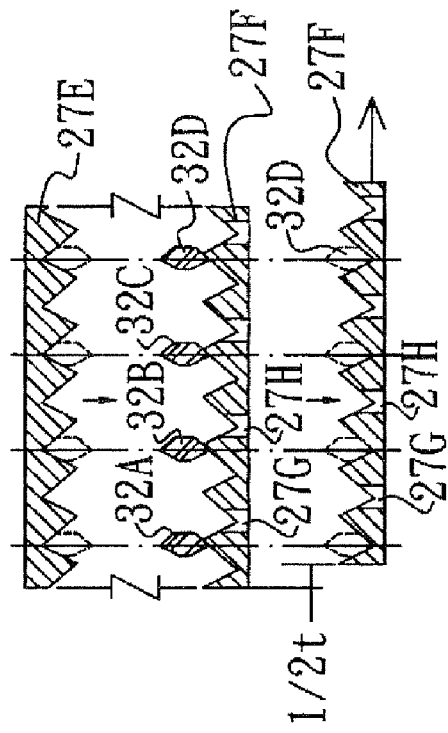
FIG. 12A is a development view illustrating relative movement between the locking blocks and the toothed crown locking collar as shown in FIG. 12.
Figure 11A:
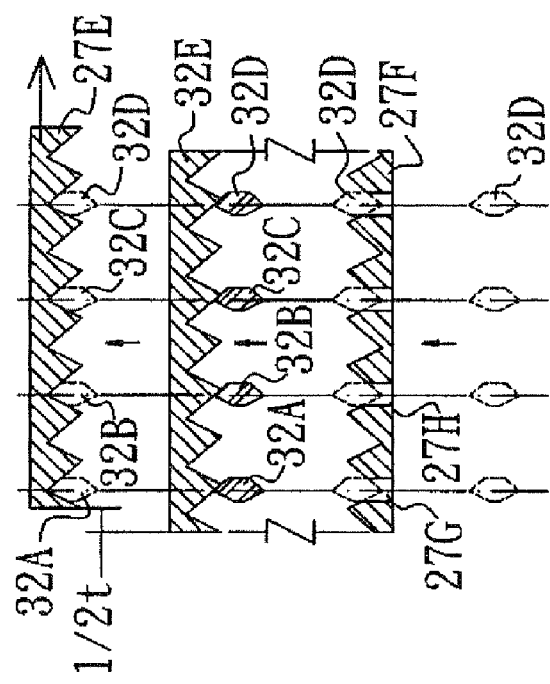
FIG. 11A is a development view illustrating relative movement between locking blocks and a toothed crown locking collar as shown in FIG. 11.

When the retained cylinder 32 approaches the uppermost position, as shown in FIG. 10, the locking blocks 32A, 32B of the retained cylinder 32 respectively passes through the channels 27G, 27H vertically corresponding thereto to enter the collar 27. As shown in FIGS. 11 and 11A, further upward pulling brings the locking blocks 32A, 32B into abutting engagement with the corresponding tooth flanks of the first toothed crown 27E, which causes the collar 27 to raise upward and circumferentially rotate in a given direction and also drives the notches 27A, 27B, 27C upward away from the bosses 28A, 28B, until the upper apexes of the locking blocks 32A, 32B reaches and engages tooth troughs of the first toothed crown 27E, where they are stopped from further upward movement. At this time, as shown in FIGS. 12 and 12A, releasing retained cylinder 32 allows the locking blocks 32A, 32B to immediately and naturally fall downward to impact and drive the corresponding tooth flanks of the second toothed crown 27F, forcing the collar 27 to further rotate in the given direction and descends to allow the locking blocks 32A, 32B to engage the teeth of the second toothed crown 27F next to the teeth that form the channels 27G, 27H to be secured therein and supported thereby, so that the retained cylinder 32 and the top retaining barrel 21 are retained together. Under this condition, even though the steel cable 11 is completely released from a user's hand and the steel cable 11 is not fastened to the winching mechanism 13 shown in FIG. 1, due to the support and securing realized with the engagement between the locking blocks 32A, 32B and the second toothed crown 27F, the retained cylinder 32 can be securely fixed and the concern about damage of the retained cylinder 32 caused by fast falling due to undesired release from the user's hand when the hand gesture of the user changes at the time that the retained cylinder 32 is pulled to the uppermost position is completely eliminated. To lower down retained cylinder 32 to inspect and maintain the camera 14 (which is not shown in this drawing, but can be found in FIG. 1) set at the bottom thereof, the process is reversed and goes from FIG. 12 to FIG. 8. With downward pulling again, the locking blocks 32A, 32B are raised and rotate the collar 27 and then get out through the channels 27G, 27H. In this way, the retained cylinder 32 can then be descend downward to allow easy and convenient inspect and maintain the output/input element 14 at the bottom of the retained cylinder 32 without an operator climbing up the post 10.

To install the camera 14, the camera 14 is first attached to the bottom of the elevation device 20 and then the winching mechanism 13 is rotated to have the steel cable 11 pulling the camera 14 upward until the retained member 30 engages and is retained by the top retaining barrel 21, whereby the camera 14 is suspended in position. To lower the camera 14 down for maintenance, the winching mechanism 13 is rotated again to pull the steel cable 11 once again for disengaging the retained member 30 from the top retaining barrel 21 to be lowered with the camera 14. Thus, maintenance can be carried out without doing post climbing.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An elevation device of monitoring camera, serving as a coupling for securing a camera that is arranged on a top end of a high suspending post and suspended on the top end of the high suspending post with a curved arrangement of a steel cable, characterized by comprising a top retaining barrel that is fixed to the top end of the high suspending post and downward fit onto a retained member, the retained member having a bottom forming a wire box, a retained cylinder, which has an opening receiving and fixing a steel cable therein, being erected on a top center of the wire box, the retained cylinder having an outer circumference on which a plurality of locking blocks is circumferentially arranged in an equally spaced manner at a location close to the opening and at an altitude, a raised cam, which has an inclined circumferential top surface, being formed on a portion of the outer circumference of the retained cylinder between the wire box and the locking blocks, the top retaining barrel comprising a locking tube set at a center thereof, the locking tube receiving therein a toothed crown locking collar at a location corresponding to a push position of the locking blocks that is defined at the time when the retained cylinder is almost fully inserted for being driven by the locking blocks in a tooth-by-tooth fashion to slide in a single given direction so as to alternately carry out locking and unlocking operation on the locking blocks, the locking tube forming a raised guide block on an inside surface thereof at a location adjacent to a bottom opening and corresponding to the inclined lower portion of the inclined circumferential top surface, whereby when the steel cable pulls the retained cylinder upward into the locking tube, the inclined circumferential top surface is guided by the guide block to correct orientation of the retained cylinder with respect to the retaining barrel so that further pulling moves the retained cylinder to an uppermost position to be retained and locked, by which the camera is selectively and readily raised and lowered by an operator staying on ground without climbing high to proceed with maintenance and repairing of the camera.

2. The elevation device according to claim 1, wherein the wire box has a top from which two positioning bars vertically extends at positions on opposite sides of and spaced from the retained cylinder by equal distance.

3. The elevation device according to claim 1, wherein the locking blocks are of a configuration having upper and lower ends that are converging and sharp, having apexes sideways shifted by a predetermined amount.

4. The elevation device according to claim 1, wherein the inclined circumferential top surface of the retained cylinder has an inclined lower portion that forms in a downward direction a vertical slot.

5. The elevation device according to claim 1, wherein a plurality of circumferentially distributed vertical ribs, which has upper and lower end that are converging and sharp, is formed on the retained cylinder at an end thereof opposite to the inclined circumferential top surface.

6. The elevation device according to claim 4, wherein a plurality of circumferentially distributed vertical ribs, which has upper and lower end that are converging and sharp, is formed on the retained cylinder at an end thereof opposite to the inclined circumferential top surface.

7. The elevation device according to claim 1, wherein the top retaining barrel is constructed by bolting a bottom of a hollow suspension locking cylinder to a connection cylinder and a pair of resilient push tubes, the suspension locking cylinder forming a mounting flange that projects from a bottom circumference of the suspension locking cylinder for being bolted to the top end of the high suspending post, the mounting flange being downward bolted to the connection cylinder and the pair of resilient push tubes in such a way that the connection cylinder is in alignment with the suspension locking cylinder to constitute together the locking tube set at the center of the top retaining barrel.

8. The elevation device according to claim 7, wherein the locking tube forms therein a support flange that projects inwardly to correspond to a bottom of the collar, the flange forming a number of circumferentially arranged raised bosses, the collar forming in a bottom thereof a plurality of circumferentially arranged notches of which the number is two times of that of the bosses and is engageable with the bosses, a spring being set between the collar and an inside wall of a top opening of the locking tube.

9. The elevation device according to claim 4, wherein the locking tube forming on an inside surface thereof at a location adjacent to a bottom opening and corresponding to the inclined lower portion of the inclined circumferential top surface a raised guide block that has upper and lower ends both being converging and sharp and has a width slidably receivable into the vertical slot.

10. The elevation device according to claim 7, wherein the resilient push tubes have openings aligning the positioning bars respectively and each sequentially receives therein a spring and a linear bearing, an inner retention ring being mounted inside the tube opening so that the linear bearing and the spring are retained and prevented from springing out of the tube opening by the inner retention ring, an end of the positioning bar being allowed to extend through the linear bearing to compress the spring.

11. The elevation device according to claim 7, wherein a downward-oriented connector having a clamp ring is fit over an outer circumference of the connection cylinder at a location close to the mounting flange.

12. The elevation device according to claim 7, wherein the toothed crown locking collar comprises a hollow collar cylinder, a first toothed crown, and a second toothed crown, which are fixed together by welding, the collar cylinder having a bottom in which notches are formed, the first toothed crown and the second toothed crown forming teeth, which have apexes that are sideways shifted, the number of the teeth of each crown being two times of the number of the locking blocks, the teeth of the first and second toothed crowns being respectively and circumferentially arranged and having such a thickness that forms a ring having a diameter sufficient to fit over an upper section of the retained cylinder, the second toothed crown forming a channel in an inside wall thereof corresponding to each alternate one of tooth troughs between the teeth for allowing the locking blocks to move therethrough, the first toothed crown being set in a reversely oriented manner to fit into and close a top end of the collar cylinder, the second toothed crown being fit into and closing a bottom end of the collar cylinder, the first toothed crown and the second toothed crown being arranged in such a way that the tooth apexes thereof are circumferentially shifted with respect to each other by a given distance, whereby the locking blocks are allowed to abut against and slide on the first and second toothed crowns for moving up and down to switch between adjacent teeth for locking engagement so as to be secured by the teeth, or to withdraw through one of the channels for releasing.

* * * * *